US012698457B2

(12) United States Patent
Tischer et al.

(10) Patent No.: US 12,698,457 B2
(45) Date of Patent: Aug. 4, 2026

(54) NON-WOVEN FABRIC CONTAINING A DISINFECTING AGENT AND METHOD FOR PRODUCING THE SAME

(71) Applicant: Glatfelter Gernsbach GmbH, Gernsbach (DE)

(72) Inventors: Thomas Tischer, Karlsruhe (DE); Jörg Kühn, Ötigheim (DE); Nicolas Déry, Ottawa (CA)

(73) Assignee: Glatfelter Gernsbach GmbH, Gernsbach (DE)

( * ) Notice: Subject to any disclaimer, the term of this patent is extended or adjusted under 35 U.S.C. 154(b) by 834 days.

(21) Appl. No.: 17/924,767

(22) PCT Filed: May 11, 2021

(86) PCT No.: PCT/EP2021/062503
§ 371 (c)(1),
(2) Date: Nov. 11, 2022

(87) PCT Pub. No.: WO2021/228868
PCT Pub. Date: Nov. 18, 2021

(65) Prior Publication Data
US 2023/0183616 A1 Jun. 15, 2023

(30) Foreign Application Priority Data

May 12, 2020 (EP) .................................... 20174270

(51) Int. Cl.

| | |
|---|---|
| *C11D 3/48* | (2006.01) |
| *A61K 8/02* | (2006.01) |
| *A61K 8/365* | (2006.01) |
| *A61K 8/41* | (2006.01) |
| *A61K 8/73* | (2006.01) |
| *A61K 8/81* | (2006.01) |
| *A61Q 17/00* | (2006.01) |
| *A61Q 19/10* | (2006.01) |
| *C11D 3/20* | (2006.01) |
| *C11D 3/22* | (2006.01) |
| *C11D 3/30* | (2006.01) |
| *C11D 3/37* | (2006.01) |
| *C11D 17/04* | (2006.01) |
| *D04H 1/26* | (2012.01) |
| *D04H 1/4258* | (2012.01) |
| *D04H 1/488* | (2012.01) |
| *D04H 1/492* | (2012.01) |
| *D06M 13/46* | (2006.01) |
| *D06M 15/03* | (2006.01) |
| *D06M 15/356* | (2006.01) |
| *D06M 15/61* | (2006.01) |
| *D06M 16/00* | (2006.01) |
| *D06M 101/06* | (2006.01) |

(52) U.S. Cl.
CPC .............. *C11D 3/48* (2013.01); *A61K 8/0208* (2013.01); *A61K 8/365* (2013.01); *A61K 8/416* (2013.01); *A61K 8/731* (2013.01); *A61K 8/817* (2013.01); *A61Q 17/005* (2013.01); *A61Q 19/10* (2013.01); *C11D 3/2086* (2013.01); *C11D 3/225* (2013.01); *C11D 3/30* (2013.01); *C11D 3/3776* (2013.01); *C11D 17/049* (2013.01); *D04H 1/26* (2013.01); *D04H 1/4258* (2013.01); *D04H 1/488* (2013.01); *D04H 1/492* (2013.01); *D06M 13/46* (2013.01); *D06M 15/03* (2013.01); *D06M 15/3562* (2013.01); *D06M 15/61* (2013.01); *D06M 16/00* (2013.01); *D06M 2101/06* (2013.01); *D10B 2201/24* (2013.01); *D10B 2401/12* (2013.01); *D10B 2509/00* (2013.01)

(58) Field of Classification Search
None
See application file for complete search history.

(56) References Cited

U.S. PATENT DOCUMENTS

| | | | |
|---|---|---|---|
| 3,905,864 | A | 9/1975 | Curry et al. |
| 6,673,761 | B2 | 1/2004 | Mitra et al. |
| 6,916,480 | B2 | 7/2005 | Anderson et al. |
| 7,709,694 | B2 | 5/2010 | Batich et al. |
| 7,741,263 | B2 | 6/2010 | Kilkenny et al. |
| 7,799,751 | B2 | 9/2010 | Kilkenny et al. |
| 8,202,832 | B2 | 6/2012 | Cheng et al. |
| 8,232,236 | B2 | 7/2012 | Jaynes et al. |
| 8,328,988 | B2 | 12/2012 | Champion et al. |
| 8,486,427 | B2 | 7/2013 | Colman et al. |
| 8,535,482 | B2 | 9/2013 | Jiang et al. |
| 8,613,836 | B2 | 12/2013 | Sealey et al. |

(Continued)

FOREIGN PATENT DOCUMENTS

| | | |
|---|---|---|
| CA | 2 736 045 A1 | 3/2003 |
| CA | 2 482 306 C | 10/2011 |

(Continued)

OTHER PUBLICATIONS

Golden Isles Fluff Fully Treated Grade 4723. Golden Isles Fluff—Technical Data Sheet. GP Cellulose, LLC. 2009.

(Continued)

*Primary Examiner* — Arti Singh-Pandey

(74) *Attorney, Agent, or Firm* — BURR & FORMAN

(57) ABSTRACT

The present invention relates to a non-woven fabric, a method for producing a non-woven fabric, a wipe or tissue and uses thereof as well as a disinfecting method, in particular against bacteria and viruses, such as coronaviruses including severe acute respiratory syndrome coronavirus 2 (SARS-COV-2). The non-woven fabric comprises pulp fibers and/or cellulosic fibers, a binder, a cationic polymer, and a disinfecting agent.

13 Claims, No Drawings

(56) References Cited

U.S. PATENT DOCUMENTS

| | | | |
|---|---|---|---|
| 8,778,386 | B2 | 7/2014 | Liu et al. |
| 8,852,399 | B2 | 10/2014 | Neal et al. |
| 10,260,201 | B2 | 4/2019 | Sealey et al. |
| 2004/0129632 | A1 | 7/2004 | Brech et al. |
| 2006/0193990 | A1 | 8/2006 | Schroeder et al. |
| 2008/0206293 | A1 | 8/2008 | Toreki et al. |
| 2009/0301519 | A1 | 12/2009 | Aubay |
| 2010/0255178 | A1 | 10/2010 | Leander et al. |
| 2011/0039054 | A1 | 2/2011 | Cabell et al. |
| 2011/0039074 | A1 | 2/2011 | Cabell et al. |
| 2011/0039469 | A1 | 2/2011 | Cabell et al. |
| 2011/0220311 | A1 | 9/2011 | Champion et al. |
| 2012/0058165 | A1 | 3/2012 | Klofta et al. |
| 2012/0301536 | A1 | 11/2012 | Charest et al. |
| 2014/0173841 | A1 | 6/2014 | Hurley et al. |
| 2014/0294749 | A1 | 10/2014 | Gentle et al. |
| 2016/0143275 | A1 | 5/2016 | Lan et al. |
| 2016/0249606 | A1 | 9/2016 | Hartgrove et al. |
| 2017/0001412 | A1 | 1/2017 | Cabell et al. |
| 2019/0082926 | A1 | 3/2019 | Dani |
| 2019/0082927 | A1 | 3/2019 | Dani |
| 2019/0085274 | A1 | 3/2019 | Dani |
| 2019/0085275 | A1 | 3/2019 | Dani |

FOREIGN PATENT DOCUMENTS

| | | |
|---|---|---|
| CA | 2 736 045 C | 7/2013 |
| CN | 101378912 B | 12/2010 |
| CN | 101394747 B | 4/2013 |
| CN | 102648238 B | 5/2016 |
| CN | 105722495 A | 6/2016 |
| CN | 106145551 A | 11/2016 |
| CN | 108135407 A | 6/2018 |
| EP | 1 059 032 A1 | 12/2000 |
| EP | 2 596 168 A1 | 5/2013 |
| EP | 3 183 969 A1 | 6/2017 |
| EP | 2 882 900 B1 | 6/2018 |
| EP | 3 403 505 A1 | 11/2018 |
| HR | P20000308A A2 | 12/2000 |
| IN | 228056 B | 1/2009 |
| IN | 2013DN00720 A | 10/2014 |
| IN | 201827026057 A | 2/2019 |
| JP | 3995231 B2 | 10/2007 |
| JP | 4056260 B2 | 3/2008 |
| JP | 5305217 B2 | 10/2013 |
| JP | 2019-500210 A | 1/2019 |
| KR | 10- 2007-0089138 A | 8/2007 |
| KR | 101376474 B1 | 3/2014 |
| MX | 2014011398 A | 11/2014 |
| TW | 201000107 A | 1/2010 |
| WO | WO 2004/001128 A1 | 12/2004 |
| WO | WO 2012/012316 A1 | 1/2012 |
| WO | WO 2014/026188 A1 | 2/2014 |
| WO | WO 2014/117964 A1 | 8/2014 |
| WO | WO 2017/108760 A1 | 6/2017 |
| WO | WO 2018/017570 A1 | 1/2018 |
| WO | WO 2018/185374 A1 | 10/2018 |
| WO | WO 2018/191488 A1 | 10/2018 |
| WO | WO 2019/023061 | 1/2019 |
| WO | WO 2020/079083 A1 | 4/2020 |

OTHER PUBLICATIONS

CF416 Fluff Pulp. International Paper/Global Cellulose Fibers-Technical Data Sheet. 2019.

AL-Adhesion II. Bicompetent PE/PP Airlaid Fibre for Fine Fabrics or Binder Fibre in Hygiene Application. ES-Fibervisions, Inc. 2019.

Valence (Pulp) Safety Data Sheet. International Paper 2021.

Vinamul Elite 25—Technical Data Sheet. Celanese—The Chemistry Inside Innovation, 2015.

NON-WOVEN FABRIC CONTAINING A DISINFECTING AGENT AND METHOD FOR PRODUCING THE SAME

CROSS-REFERENCE TO RELATED APPLICATIONS

This application is a U.S. national stage of International Application No. PCT/EP2021/062503, filed May 11, 2021, which claims priority to European Application No. 20174270.7, filed May 12, 2020, the entirety of each of which are incorporated by reference herein.

FIELD OF THE INVENTION

The present invention relates to a non-woven fabric, a method for producing a non-woven fabric, a wipe or tissue and uses thereof as well as a disinfecting method, in particular against bacteria and viruses, such as coronaviruses severe acute respiratory syndrome coronavirus 2 (SARS-COV-2).

BACKGROUND

Disposable wipes, such as wet toilet wipes or personal care wipes like baby wipes, facial wipes, sanitary wipes, kitchen towels, paper towels, cleaning tissues, etc. are very popular for cleaning the skin of human bodies or facilities in the household and elsewhere because of their comfort for consumers and efficacy in cleaning. In order to improve their cleaning efficiency and also to impart them with disinfecting properties, such wipes or tissues may be provided with disinfecting agents, for instance in the form of a lotion. Quaternary ammonium compounds, which are often also simply referred to as "Quats", may be suitably used for such disinfecting purposes. Generally, such disinfecting agents are to be released from the wipes so as to exhibit their disinfecting performance on a surface to be treated.

Wipes based on oil based synthetic fibers, such as polyethylene terephthalate (PET), polypropylene (PP), polyethylene (PE) or other polyolefins, usually show very limited bonding performance with Quats. Therefore, the release of such compounds by wiping of a surface is eased, ensuring an adequate disinfection performance with minimal Quat concentration in the lotion. However, increasing concerns about plastic contamination of the environment create an increasing demand for fully compostable/biodegradable substrates for disposable wipes and similar products.

However, when employing a bio-based sustainable cellulose based fiber substrate in a wipe, the positively charged Quats are interacting with the negatively charged natural fibers. Moreover, in order to increase the integrity and mechanical properties (such as wet/dry tensile strength) of a non-woven fabric based on natural fibers, a binder may be used. Among them, bio-based binders, such as carbohydrate- or protein-based binders, may be advantageous from an environmental point of view, but these are often also anionic at common pH conditions and may thus provide the cellulose based fiber substrate with additional negative charges. As a result, the disinfecting quaternary ammonium compounds tend to stick to the negatively charged natural fibers or the biobased binder applied and are therefore not available to serve as a disinfection agent. Rather, it may become necessary to provide the lotion applied to the substrate with a large excess of Quats to nevertheless ensure a sufficient disinfecting performance upon wiping, which is however not a satisfying solution and in particular makes it difficult, if not almost impossible, to properly adjust the disinfecting performance as desired.

Previous attempts with regard to a release of Quats include the addition of inorganic ions, such as $MgSO_4$ or KCl, to a cleaning composition which ions may compete with the cationic Quats for anionic sites on a substrate, as proposed for instance in CA 2 736 045 A1. However, by employing such inorganic ions to the disinfection lotion, the lotion gets turbid leaving wiping streams from cleaning, which is not desired. Other attempts concern the coating of in particular multilayered wipes with polyamines to increase Quat release, as proposed for instance in US 2016/0249606 A1, U.S. Pat. No. 8,486,427 B2 and WO 2018/185374 A1. However, these wipes are mainly based on synthetic, oil-based fibers, which are not sustainable or compostable and already tend to retain Quats to a much less degree than a non-woven fabric based on natural fibers, let alone further comprising a bio-based binder.

Thus, there is still a need for wipes based on substantially biodegradable or compostable substrate providing reliable and well-defined disinfecting performance without appearance issues.

Moreover, it has turned out that still nowadays pathogenic microorganisms such as bacteria and viruses may pose a tremendous risk for human health, as most recently evident from the severe acute respiratory syndrome coronavirus 2 (SARS-COV-2) and the disease Covid-19 caused by this virus, in particular in view of its fast spreading. There is therefore a strong desire for disinfecting surfaces, such as of articles, which are contacted by different people and may therefore be a source for smear infections, but also of the human skin, such as of hands and face, so as to prevent the transmission or at least slow down the spreading of pathogens, such a coronaviruses, as much as possible.

OBJECTS OF THE INVENTION

The present invention aims at overcoming the above described problems and drawbacks. Thus, it may be an object of the present invention to provide a substantially biodegradable or compostable non-woven fabric suitable for disposable applications, such as wipes or tissues, providing a reliable and well-defined disinfecting performance without appearance issues and which may in particular help to prevent the transmission or at least slow down the spreading of pathogenic microorganisms, such as coronaviruses including SARS-COV-2, as much as possible.

SUMMARY OF THE INVENTION

The present inventors have made diligent studies and have found that the release of a disinfecting agent, such as a quaternary ammonium compound, from a wipe or tissue based on a non-woven fabric mainly comprising natural fibers, such as pulp fibers and/or cellulosic fibers, and strengthened by a bio-based, typically anionic binder may be increased and properly adjusted/controlled, despite of the negatively charged or polarized chemical groups of such a substantially biodegradable or compostable non-woven fabric, by means of a cationic chemical agent, more specifically a cationic polymer, which may be capable of firmly adhering to the substantially biodegradable or compostable non-woven fabric. Without wishing to be bound by any theory, the inventors assume that the cationic polymer may hereby efficiently mask the negatively charged or polarized chemical groups of the substantially biodegradable or compostable non-woven fabric so that the positively charged disinfecting agent may be shielded from the negatively charged groups of the non-woven fabric and may thus be easily released from the fabric upon wiping. The inventors have surprisingly found that the cationic polymer may hereby firmly adhere to the fibers and/or binder of the non-woven fabric, for instance by a plurality of ionic bonds or ionic interactions, to such an extent that the cationic polymer may generally not be removed therefrom by water or wiping, so that it may be substantially avoided that released quaternary ammonium compounds may be captured again by the wipes when repeatedly wiping over a surface to be disinfected. As a result, a reliable and well-defined disinfecting performance without appearance issues may be achieved and since disinfecting agents, such as quaternary ammonium compound, which may additionally exhibit surface-active properties, are typically also effective against viruses having a virus envelope, such as coronaviruses, an important contribution against the transmission and spreading of severe acute respiratory syndrome coronavirus 2 (SARS-COV-2) and similar viruses, such as potential future variants or mutations thereof, may be provided.

Accordingly, the present invention relates to a (substantially biodegradable) non-woven fabric comprising pulp fibers and/or cellulosic fibers, a binder, a cationic polymer, and a disinfecting (antimicrobial) agent, in particular a cationic disinfecting agent.

The present invention further relates to a method for producing a (substantially biodegradable) non-woven fabric, comprising (a) forming a fibrous web from pulp fibers and/or cellulosic fibers, (b) optionally entangling at least a part of the pulp fibers and/or cellulosic fibers with each other by subjecting the fibrous web to a water-jet treatment or needle punching treatment; and (c) drying the optionally entangled fibrous web, wherein the method further comprises applying a binder to the optionally entangled fibrous web prior to drying the optionally entangled fibrous web, applying a cationic polymer to the optionally entangled fibrous web prior to and/or after drying the optionally entangled fibrous web, applying a (for instance cationic) disinfecting agent to the optionally entangled fibrous web after drying the optionally entangled fibrous web, wherein at least part of the cationic polymer is applied not later than (preferably prior to) the disinfecting agent to the optionally entangled fibrous web.

In addition, the present invention relates to a (substantially biodegradable) non-woven fabric obtainable by a method for producing a non-woven fabric as described herein.

Moreover, the present invention relates to a wipe or tissue comprising or consisting of the (substantially biodegradable) non-woven fabric as described herein.

Still further, the present invention relates to a method of disinfecting (microbial decontaminating of) a surface (such as of an article, human or animal skin), the method comprising contacting the surface with a wipe or tissue as described herein.

Thus, the present invention may also relate to the use of a wipe or tissue as described herein for disinfecting (microbial decontamination of) a surface (such as of an article, human or animal skin) to be treated.

Moreover, the present invention relates to the use of a wipe or tissue as described herein for controlling microbial growth, in particular of bacteria and viruses, on a surface (to be treated), in particular for deactivating viruses.

Thus, the present invention may also relate to the use of a wipe or tissue as described herein for reducing a microbial load, in particular a bacterial and/or viral load, on a surface to be treated.

Other objects and many of the attendant advantages of embodiments of the present invention will be readily appreciated and become better understood by reference to the following detailed description of embodiments.

DETAILED DESCRIPTION OF THE INVENTION

Hereinafter, details of the present invention and other features and advantages thereof will be described. However, the present invention is not limited to the following specific descriptions, but they are rather for illustrative purposes only.

It should be noted that features described in connection with one exemplary embodiment or exemplary aspect may be combined with any other exemplary embodiment or exemplary aspect, in particular features described with any exemplary embodiment of a non-woven fabric may be combined with any other exemplary embodiment of a non-woven fabric, with any exemplary embodiment of a method for producing a non-woven fabric, with any exemplary embodiment of a wipe or tissue, with any exemplary embodiment of a method of disinfecting, with any exemplary embodiment of a use and vice versa, unless specifically stated otherwise.

Where an indefinite or definite article is used when referring to a singular term, such as "a", "an" or "the", a plural of that term is also included and vice versa, unless specifically stated otherwise, whereas the word "one" or the number "1", as used herein, typically means "just one" or "exactly one".

The expression "comprising", as used herein, includes not only the meaning of "comprising", "including" or "containing", but may also encompass "consisting essentially of" and "consisting of".

Unless specifically stated otherwise, the expression "at least a part of", as used herein, may mean at least 5% thereof, in particular at least 10% thereof, in particular at least 15% thereof, in particular at least 20% thereof, in particular at least 25% thereof, in particular at least 30% thereof, in particular at least 35% thereof, in particular at least 40% thereof, in particular at least 45% thereof, in particular at least 50% thereof, in particular at least 55% thereof, in particular at least 60% thereof, in particular at least 65% thereof, in particular at least 70% thereof, in particular at least 75% thereof, in particular at least 80% thereof, in particular at least 85% thereof, in particular at least 90% thereof, in particular at least 95% thereof, in particular at least 98% thereof, and may also mean 100% thereof.

In a first aspect, the present invention relates to a non-woven fabric, in particular a substantially biodegradable non-woven fabric.

The term "non-woven fabric", as used herein, may in particular mean a web of individual fibers which are at least partially intertwined, but not in a regular manner as in a knitted or woven fabric.

The term "biodegradable" (which may also be referred to as "compostable"), as used herein, may in particular mean that the material concerned, such as the biodegradable non-woven fabric or biodegradable fibers, complies at least with the requirements for industrial compostability, for instance in accordance with EN 13432, and preferably also with the requirements for home compostability and is most preferred also marine biodegradable. The term "marine biodegradable", as used herein, may in particular mean that the material biodegrades by more than 90% by weight within 12-month storage in sea water at min. 15° C. and exposure to daylight.

The non-woven fabric comprises pulp fibers and/or cellulosic fibers.

In an embodiment, the pulp fibers may be natural pulp fibers, in particular pulp fibers of natural origin, such as softwood pulp fibers or hardwood pulp fibers. Pulp may in particular denote a (lignocellulosic) fibrous material prepared by chemically or mechanically separating cellulose fibers from wood or the like, such as by a kraft process (sulfate process). An example for a suitable pulp is Valence™ pulp from International Paper, but other pulps are of course suitable as well.

In an embodiment, the pulp fibers may have an average fiber length of from 1.0 mm to 4.0 mm, for instance from 1.5 mm to 3.5 mm, such as from 2.0 mm to 3.2 mm.

In an embodiment, the pulp fibers may have a fiber coarseness of from 0.3 to 3.5 dtex, such as from 0.6 to 2.5 dtex.

In an embodiment, the pulp fibers may be comprised in an amount of from 50 to 100 wt.-%, such as in an amount of from 60 to 98 wt.-%, such as in an amount of from 70 to 95 wt.-%, such as in an amount of from 75 to 93 wt.-%, such as in an amount of from 80 to 90 wt.-% or in an amount of from 70 to 85 wt.-% (preferably 75 wt.-%), based on the total weight of the fibers of the non-woven fabric. Thus, it may be possible that the non-woven fabric may comprise only pulp fibers (i.e. 100 wt.-% of the fibers) as the fibers.

In an embodiment, the non-woven fabric comprises cellulosic fibers. The term "cellulosic fibers", as used herein, may in particular denote fibers based on cellulose, in particular modified or regenerated cellulose fibers, such as fibers prepared from cellulose, or cellulose derivates, such as ethyl cellulose, cellulose acetate and the like. The term "regenerated cellulose fibers", as used herein, may in particular denote manmade cellulose fibers obtained by a solvent spinning process.

In an embodiment, the regenerated cellulose fibers may be selected from the group consisting of viscose (rayon) or lyocell (tencel).

Viscose is a type of solvent spun fiber produced according to the viscose process typically involving an intermediate dissolution of cellulose as cellulose xanthate and subsequent spinning to fibers.

Lyocell is a type of solvent spun fiber produced according to the aminoxide process typically involving the dissolution of cellulose in N-methylmorpholine N-oxide and subsequent spinning to fibers.

In an embodiment, the cellulosic fibers may have an average fiber length of from 3 mm to 80 mm, for instance an average fiber length of from 5 to 70 mm, for instance an average fiber length of from 10 to 65 mm, for instance an average fiber length of from 15 to 60 mm, for instance an average fiber length of from 18 to 50 mm, such as an average fiber length of from 20 to 40 mm.

In an embodiment, the cellulosic fibers may have an average fiber length of from 3 mm to 10 mm. This may be advantageous, in particular when the non-woven fabric is prepared by an air-laid process.

In an embodiment, the cellulosic fibers may have an average fiber length of from 3 mm to 8 mm. This may be advantageous, in particular when the non-woven fabric is prepared by a wet-laid process.

In an embodiment, the cellulosic fibers may have an average fiber length of from 15 mm to 60 mm. This may be advantageous, in particular when the non-woven fabric is prepared by a carding or carded-spunlace process.

In an embodiment, the cellulosic fibers may have a fiber coarseness of from 0.5 to 4.0 dtex, such as from 1.0 to 2.5 dtex.

In an embodiment, the cellulosic fibers may be comprised in an amount of from 0 to 50 wt.-%, such as in an amount of from 2 to 40 wt.-%, such as in an amount of from 5 to 30 wt.-%, such as in an amount of from 7 to 25 wt.-%, such as in an amount of from 10 to 20 wt.-%, based on the total weight of the fibers of the non-woven fabric.

In an embodiment, the non-woven fabric further comprises biodegradable polymer fibers (which may sometimes also be referred to as "synthetic biodegradable fibers"). Also biodegradable polymer fibers typically have polarized chemical groups, such as ester groups, to which a cationic polymer may adhere, thereby masking the same and suppressing interactions with a disinfecting agent. Suitable examples include polylactic acid (PLA), polyhydroxyalkanoate (PHA), polybutylene succinate (PBS) or polybutylene adipate terephthalate (PBAT) fibers as well as combinations or blends thereof. The biodegradable polymer fibers may be comprised for instance in an amount of from 0 to 30 wt.-%, such as in an amount of from 1 to 25 wt.-%, such as in an amount of from 2 to 20 wt.-%, such as in an amount of from 3 to 15 wt.-%, such as in an amount of from 5 to 10 wt.-%, based on the total weight of the fibers of the non-woven fabric.

In an embodiment, substantially all fibers comprised in the non-woven fabric are the pulp fibers and/or cellulosic fibers and the optional biodegradable polymer fibers. Thus, substantially all fibers comprised in the non-woven fabric may be biodegradable fibers. In other words, it may be possible that the non-woven fabric does substantially not comprise any other fibers than biodegradable fibers, in particular no other fibers than the pulp fibers and/or cellulosic fibers described herein. With regard to embodiments comprising "substantially no other fibers than biodegradable fibers", other fibers than biodegradable fibers, if any, may still be present in relatively minor amounts of up to 10, up to 5, up to 3, up to 2, or up to 1 wt.-% based on the total weight of the non-woven fabric.

In an embodiment, at least a part of the pulp fibers and/or cellulosic fibers and of the optional biodegradable polymer fibers is entangled with each other.

The term "entangled", as used herein, may in particular mean that the fibers are at least partly intertwined with each other, thereby imparting strength, such as tear strength or tensile strength, to the non-woven fabric. Entangling of the fibers might in particular be achieved by a treatment of a fibrous web with water jets, as will be explained in further detail below, which may also be referred to as "hydroentanglement" or "spunlacing" and the entangled fibers may thus also be referred to as "hydroentangled fibers" or "spunlaced fibers". Alternatively, entangling of the fibers might be achieved by needle punching where the fibers are mechanically intertwined by means of needles.

In an embodiment, the non-woven fabric is a single-layer non-woven fabric, i.e. not a multi-layer non-woven fabric with distinct or different layers. In other words, the non-woven fabric preferably comprises or consists of one single layer wherein the pulp fibers and/or cellulosic fibers are comprised.

The non-woven fabric further comprises a binder. The term "binder", as used herein, may in particular denote a chemical compound that is able to bind (e.g. by forming covalent bonds, by ionic interactions or the like) to two or more fibers, thereby interconnecting the fibers, resulting in an increased tensile strength of the web or fabric. The binder may in particular be a particulate binder, i.e. a binder in the form of particles (characterized for instance by an average particle size), but the binder may also be in a fibrous form, i.e. a binder fiber, and/or applied in the form of a dispersion, i.e. a binder dispersion.

In an embodiment, the binder is an anionic binder. In other words, the binder may be a chemical compound that has anionic moieties, i.e. is (at least partly) negatively charged, in particular at common pH conditions, such as in a pH range of from 3 to 10, as determined in accordance with DIN 53124:1998-08. In particular, such anionic moieties of the binder (or at least a part thereof) may still be present in the non-woven fabric after binding to the fibers, thereby rendering the non-woven fabric even more negatively charged.

In an embodiment, the binder (in particular a particulate binder) is selected from the group consisting of carbohydrate-based binders, such as pectin, starch and cellulose derivatives, in particular blends of carboxymethylcellulose and an organic polyprotic acid (such as citric acid), and protein-based binders. Combinations of two or more thereof may also be applied. The term "cellulose derivatives", as used herein, may in particular denote chemically modified (for instance methylated, ethylated, hydroxypropylated, acetylated and/or carboxylated) cellulose compounds, and may in particular include cellulose ethers and cellulose esters, such as methylcellulose, ethylcellulose, hydroxyethyl cellulose, hydroxypropyl cellulose, carboxymethyl cellulose or cellulose acetate. Further suitable binders are disclosed in WO 2014/117964 A1, the disclosure of which is incorporated herein by reference. A particularly suitable binder for imparting desired mechanical properties, such as an increased tensile strength of the non-woven fabric, has proven to be a combination of carboxymethylcellulose (CMC) and citric acid (or salts thereof, such as its sodium salt).

In an embodiment, the binder (in particular in case of a particulate binder) may be comprised in an amount of from 0.05 to 5 wt.-%, such as in an amount of from 0.1 to 4 wt.-%, such as in an amount of from 0.25 to 3 wt.-%, such as in an amount of from 0.5 to 2.5 wt.-%, based on the total weight of the non-woven fabric.

In an embodiment, the binder comprises a binder fiber, in particular a bicomponent fiber, such as a bicomponent fiber of the sheath-core type. Bicomponent fibers are composed of two sorts of polymers having different physical and/or chemical characteristics, in particular different melting characteristics. A bicomponent fiber of the sheath-core type typically has a core of a higher melting point component and a sheath of a lower melting point component. For instance, the sheath may comprise polyethylene (PE) and the core may comprise polypropylene (PP). As another example, the sheath may comprise a polyolefin (e.g. a copolyolefin) and the core may comprise polyethylene terephthalate (PET). The bicomponent fiber may have an average fiber length of from 3 mm to 8 mm, such as about 6 mm, and a fiber coarseness of from 1.0 to 2.5 dtex, such as about 1.7 dtex. The binder fiber, in particular the bicomponent fiber, may be comprised in an amount of from 15 to 30 wt.-%, such as in an amount of from 17.5 to 27.5 wt.-%, such as in an amount of from 20 to 25 wt.-%, based on the total weight of the non-woven fabric.

In an embodiment, the binder comprises a binder dispersion or more specifically the binder may be applied as a binder dispersion. For instance, the binder dispersion may comprise a latex binder, such as a copolymer based on vinyl acetate and ethylene, i.e. an ethylene-vinyl acetate (EVA) copolymer. In case of a binder dispersion, the binder may be comprised in an amount of from 5 to 20 wt.-%, such as in an amount of from 7 to 18 wt.-%, such as in an amount of from 9 to 17 wt.-%, based on the total weight of the non-woven fabric.

In an embodiment, the non-woven fabric may further comprise a wet-strength agent. The term "wet-strength agent", as used herein, may in particular denote an agent that improves the tensile strength of the non-woven web in the wet state. In particular, it may be preferred that the wet-strength agent is biodegradable. However, it may also be possible to use a non-biodegradable wet-strength agent (for instance in small amounts not negatively impacting the biodegradability/compostability) which may significantly increase the wet tensile strength of the non-woven fabric. In an embodiment, the optional wet-strength agent may comprise an epichlorohydrin resin, such as a polyamine-polyamide-epichlorohydrin resin. In an embodiment, the optional wet-strength agent may be comprised in an amount of from 0.1 to 3 wt.-%, such as in an amount of from 0.2 to 2 wt.-%, such as in an amount of from 0.35 to 1.5 wt.-%, such as in an amount of from 0.5 to 1 wt.-%, based on the total weight of the non-woven fabric.

A wet-strength agent within the meaning of the present application and a binder within the meaning of the present application may in particular be distinguished by the time of its application. A wet-strength agent is typically added to a fiber blend prior to formation of a fibrous web or textile structure. For instance, a wet-strength agent may be applied into or prior to a head box of a paper-making machine. A binder (in particular in case of a particulate binder or a binder dispersion) is typically applied after formation of a fibrous web or textile structure and may even be applied after an entanglement of the fibrous web, if applicable. For instance, a binder may be applied or added to an entangled fibrous web, but preferable prior to drying the entangled web. It is also feasible to apply the binder after drying the hydroentangled web, but this would be less efficient due to the necessity of drying the web twice.

The non-woven fabric further comprises a cationic polymer. In other words, the cationic polymer may be a polymeric compound (for instance a compound having an average molecular weight (Mw) of more than 5000 g/mol, in particular at least 10000 g/mol or even at least 100000 g/mol) that has cationic moieties, i.e. is (at least partly) positively charged, in particular at common pH conditions, such as in a pH range of from 3 to 10, as determined in accordance with DIN 53124:1998-08.

In an embodiment, the cationic polymer is configured for masking negative charges of the pulp and/or cellulosic fibers and/or of the binder.

In an embodiment, the cationic polymer is selected from the group consisting of ammonium compounds, in particular polydiallyldimethylammonium chloride (poly-DADMAC) and poly(acrylamide-co-diallyldimethylammonium chloride) (PAM-DADMAC), polyamines, cationic carbohydrates (such as cationic starch, cationic CMC) and poly (amino saccharides) (such as chitosan). Combinations of two or more thereof may also be applied. In particular, polydiallyldimethylammonium chloride (poly-DADMAC) has proven to be particularly suitable for efficiently masking negatively charged or polarized chemical groups of the fibers and/or the binder of the non-woven fabric and thus for shielding the positively charged disinfecting agent from the negatively charged groups of the non-woven fabric and additionally may firmly adhere to the fibers and/or binder of the non-woven fabric to such an extent that the poly-DADMAC may generally not be removed therefrom by water or wiping.

In an embodiment, the cationic polymer may be comprised in an amount of from 0.1 to 10 wt.-%, such as in an amount of from 0.2 to 8 wt.-%, such as in an amount of from 0.5 to 5 wt.-%, such as in an amount of from 1 to 4 wt.-%, based on the total weight of the non-woven fabric.

The non-woven fabric further comprises a disinfecting agent, which may also be denoted an antimicrobial agent. The term "disinfecting agent" or "antimicrobial agent", as used herein, may in particular denote a compound or mixture of compounds having an inhibitory (or antagonistic) effect on the growth of microorganisms, that is, compounds that are capable of at least reducing the growth rate (e.g. bacteriostatic agents with respect to controlling the growth of bacteria and/or virostatic agents with respect to controlling the replication of viruses) as well as compounds that cause toxic effects (e.g. bactericide agents killing bacteria and/or virucide agents killing viruses). In a particular preferred embodiment, the disinfecting agent may be effective against coronaviruses (family Coronaviridae), such as severe acute respiratory syndrome coronavirus 2 (SARS-COV-2) as well as variants and mutations thereof.

In an embodiment, the disinfecting agent comprises a quaternary ammonium compound. A quaternary ammonium compound may in particular denote an organic compound having a nitrogen atom with four non-hydrogen substituents, such as alkyl and/or aryl groups, and thus being permanently positively charged, irrespective of the pH value in its surroundings. The quaternary ammonium compound suitable for use in the present invention is not particularly limited and any quaternary ammonium compound exhibiting disinfecting and/or antimicrobial properties may be used. Preferably, the quaternary ammonium compound may also have surface-active properties which may render the disinfecting agent particularly effective against viruses having a virus envelope, such as coronaviruses. Suitable examples of the quaternary ammonium compound include alkyltrimethylammonium salts (such as cetyltrimethylammonium bromide), dialkyldimethylammonium salts (such as didecyldimethylammonium chloride), alkyldimethylbenzylammonium salts (such as benzalkonium chloride and cetalkonium chloride), alkyl pyridinium salts (such as cetylpyridinium chloride), benzethonium chloride and methylbenzethonium chloride. Combinations of two or more thereof may also be applied.

In an embodiment, the disinfecting agent may be comprised in an amount of from 0.1 to 20 wt.-%, such as in an amount of from 0.2 to 15 wt.-%, such as in an amount of from 0.3 to 10 wt.-%, such as in an amount of from 0.4 to 5 wt.-%, such as in an amount of from 0.5 to 1 wt.-%, based on the total weight of the non-woven fabric.

In an embodiment, the non-woven fabric may be treated (impregnated) with a liquid or a lotion. In other words, the non-woven fabric may further comprise a liquid or a lotion. In such situation, the non-woven fabric may in particular represent a wet wipe or wet tissue. The liquid or the lotion is not particularly limited, and any liquid or lotion customary in the field of wet wipes or wet tissues may be applied. Typically, the liquid or the lotion may comprise a solvent, such as water, an alcohol, or mixtures thereof, surfactants or detergents, skin care agents, emollients, humectants, perfumes, preservatives etc. depending on the intended use. Preferably, the liquid or the lotion comprises the disinfecting agent. Thus, the disinfecting agent may be applied to the non-woven fabric as and/or by means of a liquid or a lotion.

In an embodiment, the binder comprises a blend of carboxymethylcellulose and citric acid, the cationic polymer comprises polydiallyldimethylammonium chloride (poly-DADMAC), and the disinfecting agent comprises a quaternary ammonium compound. Such a combination has proven particularly suitable for solving the object of the present invention.

In an embodiment, the non-woven fabric may have a grammage or basis weight of from 20 to 150 $g/m^2$, such as from 25 to 125 $g/m^2$, such as from 30 to 100 $g/m^2$, such as from 35 to 80 $g/m^2$, such as from 40 to 60 $g/m^2$, such as from 45 to 50 $g/m^2$.

In a second aspect, the present invention relates to a method for producing a (substantially biodegradable) non-woven fabric, in particular of a (substantially biodegradable) biodegradable non-woven fabric as described herein.

The method comprises the steps of:
- (a) forming a fibrous web from pulp fibers and/or cellulosic fibers (and optional other fibers);
- (b) optionally entangling at least a part of the pulp fibers and/or cellulosic fibers with each other by subjecting the fibrous web to a water-jet treatment or needle punching treatment; and
- (c) drying the optionally entangled fibrous web.

The method further comprises the following, which may be carried out in common and/or separate steps:
- (i) applying a binder to the optionally entangled fibrous web prior to drying the optionally entangled fibrous web,
- (ii) applying a cationic polymer to the optionally entangled fibrous web prior to and/or after drying the optionally entangled fibrous web, and
- (iii) applying a (for instance cationic) disinfecting agent to the optionally entangled fibrous web after drying the optionally entangled fibrous web.

At least part of the cationic polymer is applied not later than (preferably prior to) the disinfecting agent to the optionally entangled fibrous web. By taking this measure, it may be substantially avoided that the (typically cationic) disinfecting agent comes into contact with the fibrous web (bearing negatively charged or polarized chemical groups stemming from the pulp and/or cellulosic fibers and/or of the binder) and may thus bond to the fibrous web before the negative charges of the pulp and/or cellulosic fibers and/or of the binder may be substantially masked by the cationic polymer, thereby substantially shielding the positively charged disinfecting agent from the negatively charged groups of the non-woven fabric so that the disinfecting agent may be appropriately released from the fabric upon wiping.

In step (a), the fibrous web may be prepared for instance by a conventional wet-laid process using a wet-laid machine, such as an inclined wire or flat wire machine, or a dry-forming air-laid non-woven manufacturing process. A conventional wet-lay process is described for instance in US 2004/0129632 A1, the disclosure of which is incorporated herein by reference. A suitable dry-forming air-laid non-woven manufacturing process is described for instance in U.S. Pat. No. 3,905,864, the disclosure of which is incorporated herein by reference. Thus, the fibrous web may be formed for instance by a wet-laid process or an air-laid process. The fibrous web may however also be formed by a carding or carded-spunlace process.

In an embodiment, the fibrous web is formed by a wet-laid process. In another embodiment, the fibrous web is formed by an air-laid process. Also a combination of a carding process or an airlay process combined with an airlaid process is suitable for forming a layer of cellulosic fibers combined with a layer of pulp fibers.

The fiber blend used for forming the fibrous web comprises pulp fibers and/or cellulosic fibers and may optionally further comprise a wet-strength agent and/or other fibers, such as biodegradable polymer fibers and/or binder fibers.

In the optional step (b), at least a part of the pulp fibers and/or cellulosic fibers are entangled with each other by subjecting the fibrous web to a water-jet treatment or needle punching treatment. The term "water-jet treatment", as used herein, may in particular mean a process of mechanically entangling fibers by giving the fibrous web an impact with jets of water. Water-jet treatment may also be referred to as hydroentanglement or spunlacing. Water-jet treatment typically involves the ejection of fine, high pressure jets of water from a plurality of nozzles on a fibrous web provided on a conveyor belt or forming-wire. The water jets penetrate the web, hit the belt where they may be reflected and pass again the web causing the fibers to entangle. Thus, by subjecting the fibrous web to the water-jet treatment, the fibers are entangled, in particular hydroentangled. Alternatively, entangling of the fibers might be achieved by needle punching where the fibers are mechanically intertwined by means of needles.

In an embodiment, a binder is applied to the optionally entangled fibrous web prior to drying the optionally entangled fibrous web. The binder may be applied in the form of a solution or dispersion to the optionally entangled fibrous web. For instance, the binder may be applied by spraying or other means of liquid application like a size-press, foulard or other. If the binder comprises a binder fiber, the binder fiber may already be added to the fiber blend (fiber furnish) used for forming the fibrous web in step (a) and subsequently thermobonded, for instance in step (c).

In an embodiment, a cationic polymer is applied to the optionally entangled fibrous web prior to and/or after drying the optionally entangled fibrous web. The cationic polymer may be applied similar to the binder and it may even be possible to apply the cationic polymer together with the binder, for instance as a solution or dispersion comprising the binder and (at least part of) the cationic polymer. It may however also be possible to apply the cationic polymer after drying the optionally entangled fibrous web, for instance before applying the disinfecting agent. It might however even be possible to apply the cationic polymer (at least a part thereof) together with the disinfecting agent, for instance by adding (at least part of) the cationic polymer to a liquid or lotion containing the disinfecting agent and applying such liquid or lotion to the dried, optionally entangled fibrous web.

In step (c), the drying of the optionally entangled fibrous web may preferably be carried out such that the binder is cured (for instance, thermobonded in case of binder fibers) and/or water (if present, such as in case of a wet-laid process or if subjected to water-jet treatment) is substantially removed from the optionally entangled fibrous web. In particular, the drying is preferably carried out at a (sufficiently high) temperature to cure the binder and optionally the wet-strength agent and/or to substantially remove water, for instance at a temperature of more than 80° C., such as more than 100° C., such as more than 120° C., such as more than 140° C., such as more than 180° C.

After step (c) of drying the optionally entangled fibrous web, a disinfecting agent is applied, for instance in the form of a liquid or lotion. Since a cationic polymer has been applied prior to or at least not later than the disinfecting agent, negatively charged or polarized chemical groups of the fibrous web stemming from the pulp and/or cellulosic fibers and/or of the binder may be substantially masked by the cationic polymer when the (typically positively charged) disinfecting agent is applied, so that the disinfecting agent is substantially shielded from the negatively charged groups of the fabric and the disinfecting agent may be appropriately released from the fabric when used, such as upon wiping or disinfecting a surface.

Exemplary embodiments of a method for producing a non-woven fabric include for instance the following sequences A) to D) of process steps:

A)
1. (a) forming a fibrous web
2. optionally (b) entangling fibers
3. (i) applying a binder
4. (c) drying
5. (ii) applying a cationic polymer
6. (iii) applying a disinfecting agent B)
1. (a) forming a fibrous web
2. optionally (b) entangling fibers
3. (i) applying a binder
4. (c) drying
5. (ii)+(iii) applying a cationic polymer and a disinfecting agent (for instance in a common lotion)

C)
1. (a) forming a fibrous web
2. optionally (b) entangling fibers
3. (i)+(ii) applying a binder and a cationic polymer (for instance in a common solution)
4. (c) drying
5. (iii) applying a disinfecting agent D)
1. (a) forming a fibrous web
2. optionally (b) entangling fibers
3. (i)+(ii) applying a binder and a part of the cationic polymer (for instance in a common solution)
4. (c) drying
5. (ii)+(iii) applying the remaining part of the cationic polymer and a disinfecting agent (for instance in a common lotion)

In a third aspect, the present invention relates to a (substantially biodegradable) non-woven fabric obtainable by a method for producing a non-woven fabric as described herein. In particular, a non-woven fabric obtainable by a method for producing a non-woven fabric as described herein may have any of the properties or features of a non-woven fabric according to the first aspect, as described in the foregoing.

In a fourth aspect, the present invention relates to a wipe or tissue comprising or consisting of the non-woven fabric as described herein. In particular, the non-woven fabric according to the present invention may be usable as a wipe or a tissue.

In an embodiment, the wipe or tissue may be a wet wipe or wet tissue. For instance, the wet wipe may be treated with a liquid or a lotion, as described in further detail above.

In an embodiment, the wipe or tissue is selected from the group consisting of facial wipes, cosmetic wipes, baby wipes, sanitary wipes, kitchen towel, paper towel, handkerchiefs (facial tissue), cleaning tissue, cleansing tissue, floor mop and hard surface cleaning wipe.

In a fifth aspect, the present invention relates to a method of disinfecting (microbial decontaminating of) a surface (such as of an article, human or animal skin), the method comprising contacting (in particular wiping, such as once, twice or for a plural times) the surface with a wipe or tissue as described herein.

Thus, the present invention may also relate to the use of a wipe or tissue as described herein for disinfecting (microbial decontamination of) a surface (such as of an article, human or animal skin) to be treated, for instance by contacting (in particular wiping) the surface with the wipe or tissue.

In a sixth aspect, the present invention relates to the use of a wipe or tissue as described herein for controlling microbial growth, in particular of bacteria and viruses, on a surface (to be treated), in particular for deactivating viruses. Thus, the present invention may also relate to the use of a wipe or tissue as described herein for reducing a microbial load, in particular a bacterial and/or viral load, on a surface to be treated.

The term "controlling microbial growth", as used herein, denotes any activity for completely inhibiting or at least reducing the growth and/or replication of microorganisms such as bacteria, archaea, yeasts, fungi, viruses, and the like, in a given environment. The term "reducing", as used herein, denotes any decrease in an microorganism's growth and/or replication; for example, a decrease of at least 5%, 10%, 15%, 20%, 25%, 30%, 40%, 50%, 60%, 70%, 80%, 85%, 90% or 95% as compared to control conditions (i.e. in the absence of antimicrobial agents according to the present invention).

The term "microorganisms", as used herein, denotes any microscopic organism (i.e. organisms too small to be seen by the naked human eye) including both prokaryotic and eukaryotic organism as well as both single cell-organisms and multi-cellular organisms. Examples of microorganisms include inter alia bacteria, archaea (archaebacteria), fungi, yeasts, and viruses.

In an embodiment, the viruses include RNA viruses and/or viruses having a virus envelope, in particular coronaviruses (family Coronaviridae).

In an embodiment, the viruses include severe acute respiratory syndrome coronavirus 2 (SARS-COV-2) as well as variants or mutations thereof.

While the present invention has been described in detail by way of specific embodiments and examples, the invention is not limited thereto and various alterations and modifications are possible, without departing from the scope of the invention.

The invention claimed is:

1. A non-woven fabric comprising:
pulp fibers and/or cellulosic fibers,
a binder, wherein the binder comprises an anionic binder selected from the group consisting of carbohydrate-based binders, protein-based binders and mixtures thereof,
a cationic polymer selected from the group consisting of ammonium compounds, polyamines, cationic carbohydrates, poly(amino saccharides) and mixtures thereof, and
a disinfecting agent, wherein the disinfecting agent comprises a quaternary ammonium compound.

2. The non-woven fabric according to claim 1, wherein at least one of the following is fulfilled:
wherein the pulp fibers are comprised in an amount of from 50 to 100 wt.-% based on the total weight of the non-woven fabric; and/or
wherein the cellulosic fibers are comprised in an amount of from 0 to 50 wt.-% based on the total weight of the non-woven fabric; and/or wherein the cellulosic fibers comprise regenerated cellulose fibers; and/or
wherein the non-woven fabric further comprises biodegradable polymer fibers; and/or
wherein substantially all fibers comprised in the non-woven fabric are the pulp fibers and/or cellulosic fibers and the optional biodegradable polymer fibers; and/or
wherein at least a part of the pulp fibers and/or cellulosic fibers and of the optional biodegradable polymer fibers is entangled with each other; and/or
wherein the non-woven fabric is a single-layer non-woven fabric.

3. The non-woven fabric according to claim 1,
wherein the binder is selected from the group consisting of pectin, starch, cellulose derivatives, and mixtures thereof; and/or
wherein the binder further comprises a binder fiber; and/or
wherein the binder further comprises a binder dispersion.

4. The non-woven fabric according to claim 1, wherein the cationic polymer is configured for masking negative charges of the pulp fibers and/or the cellulosic fibers and/or the binder.

5. The non-woven fabric according to claim 1, wherein the cationic polymer is selected from the group consisting of polydiallyldimethylammonium chloride (poly-DADMAC) and poly(acrylamide-co-diallyldimethylammonium chloride) (PAM-DADMAC), and mixtures thereof.

6. The non-woven fabric according to claim 1, wherein the binder comprises a blend of carboxymethylcellulose and citric acid, and the cationic polymer comprises polydiallyldimethylammonium chloride (poly-DADMAC.

7. A wipe or tissue comprising or consisting of the non-woven fabric according to claim 1.

8. The non-woven fabric according to claim 1, wherein:
the non-woven fabric comprises pulp fibers in an amount of from 50 to 100 wt.-% based on the total weight of the non-woven fabric,
the non-woven fabric further comprises biodegradable polymer fibers,
at least a part of the pulp fibers and a part of the biodegradable polymer fibers are entangled with each other, and
the non-woven fabric is a single-layer non-woven fabric.

9. The non-woven fabric according to claim 1, wherein:
the non-woven fabric comprises cellulosic fibers are comprised in an amount of from 0 to 50 wt.-% based on the total weight of the non-woven fabric,
the non-woven fabric further comprises biodegradable polymer fibers;
at least a part of the cellulosic fibers and a part of the biodegradable polymer fibers are entangled with each other; and
the non-woven fabric is a single-layer non-woven fabric.

10. The non-woven fabric according to claim 1, wherein the cellulosic fibers comprise regenerated cellulose fibers.

11. The non-woven fabric according to claim 1, wherein the binder is 0.05 to 5 wt % of the non-woven fabric, the cationic polymer 0.1 to 10 wt % of the non-woven fabric, and
the disinfecting agent is 0.1 to 20 wt % of the non-woven fabric.

12. The non-woven fabric according to claim 11, further comprising:
biodegradable polymer fibers in an amount ranging from 1 to 25 wt % of the total weight of all fibers of the non-woven fabric; and a biodegradable wet-strength agent in an amount ranging from 0.1 to 3 wt % of the non-woven fabric.

13. The non-woven fabric according to claim 12, wherein the non-woven fabric is a single-layer non-woven fabric.

* * * * *